(12) United States Patent
Liu

(10) Patent No.: US 6,562,973 B1
(45) Date of Patent: May 13, 2003

(54) METHOD FOR MAKING LATE TRANSITION METAL CATALYSTS FOR OLEFIN POLYMERIZATION

(75) Inventor: Jia-Chu Liu, Mason, OH (US)

(73) Assignee: Equistar Chemicals, LP, Houston, TX (US)

(*) Notice: Subject to any disclaimer, the term of this patent is extended or adjusted under 35 U.S.C. 154(b) by 0 days.

(21) Appl. No.: 09/930,629

(22) Filed: Aug. 15, 2001

(51) Int. Cl.⁷ .......................... C07F 15/00; B01J 31/00
(52) U.S. Cl. ..................... 546/12; 546/2; 502/167; 556/137; 556/138
(58) Field of Search ............ 546/2, 12; 502/167; 556/137, 138

(56) References Cited

U.S. PATENT DOCUMENTS

| | | | |
|---|---|---|---|
| 5,153,157 A | 10/1992 | Hlatky et al. | 502/117 |
| 5,198,401 A | 3/1993 | Turner et al. | 502/155 |
| 5,241,025 A | 8/1993 | Hlatky et al. | 526/129 |
| 5,414,180 A | 5/1995 | Geerts et al. | 585/525 |
| 5,539,124 A | 7/1996 | Etherton et al. | 548/402 |
| 5,554,775 A | 9/1996 | Krishnamurti et al. | 556/7 |
| 5,648,440 A | 7/1997 | Sugano et al. | 526/132 |
| 5,866,663 A | 2/1999 | Brookhart et al. | 526/170 |
| 5,955,555 A | 9/1999 | Bennett | 526/133 |
| 6,211,311 B1 | 4/2001 | Wang et al. | 526/131 |
| 6,414,098 B1 | 7/2002 | Engehausen et al. | 526/161 |

FOREIGN PATENT DOCUMENTS

| | | |
|---|---|---|
| WO | WO 99/12981 | 3/1999 |
| WO | Wo 01/00686 | 1/2001 |

OTHER PUBLICATIONS

*Chem. & Eng. News*, Apr. 13, 1998, p. 11.
A. Bennett, *Chemtech*, Jul. 1999, p. 24.
G. Britovsek et al., *Chem. Commun.* (1998) 849.
B. Small et al., *J. Am. Chem. Soc.* 120 (1998) 4049.
S. Ittel et al., *Chem. Rev.* 100 (2000) 1169.
L. Sacconi et al., *J. Chem. Soc. A* (1968) 1510.
G. Britovsek et al., *J. Am. Chem. Soc.* 121 (1999) 8728.

*Primary Examiner*—Porfirio Nazario-Gonzalez
(74) *Attorney, Agent, or Firm*—Jonathan L. Schuchardt

(57) ABSTRACT

Methods for making Group VIII metal bis(imine) complexes are disclosed. Each method uses a single reactor that is equipped with an internal filter to facilitate preparation and purification of the complex under an inert atmosphere. The complexes, which are useful in catalyst systems for olefin polymerization, are prepared in either one or two reaction steps. Surprisingly, the single-reactor approach to preparation and purification enables the efficient preparation of exceptionally high (>90%) yields of desirable Group VIII metal bis(imine) complexes.

22 Claims, No Drawings

METHOD FOR MAKING LATE TRANSITION METAL CATALYSTS FOR OLEFIN POLYMERIZATION

FIELD OF THE INVENTION

The invention relates to a method for making olefin polymerization catalysts. In particular, the invention relates to a high-yield method for making late transition metal complexes in a single reactor.

BACKGROUND OF THE INVENTION

"Single-site" catalysts, which include metallocenes, actively polymerize olefins to give polymers with valuable properties such as narrow molecular weight distribution and uniform comonomer distribution. While traditional metallocenes have cyclopentadienyl (Cp) ligands and/or Cp-like ligands (e.g., iridenyl, fluorenyl), a variety of non-metallocene, single-site catalysts having heteroatomic ring ligands have also been developed (see, e.g., U.S. Pat. Nos. 5,554,775 and 5,539,124).

Since the late 1990s, olefin polymerization catalysts that incorporate late transition metals (especially iron, nickel, or cobalt) and bulky α-diimine ligands (hereinafter also called "bis(imine) ligands" or "bis(imines)") have been extensively studied and described by scientists at DuPont, the University of North Carolina at Chapel Hill, and BP Chemicals. For a few examples, see Chem. & Eng. News, Apr. 13, 1998, p. 11; Chemtech, July 1999, p. 24; Chem. Commun. (1998) 849; J. Am. Chem. Soc. 120 (1998) 4049; Chem. Rev. 100 (2000) 1169; PCT Int. Publ. WO 99/12981; and U.S. Pat. Nos. 5,866,663 and 5,955,555. Similar complexes have been known much longer (see, e.g., J. Chem. Soc., Part A (1968) 1510), but olefin polymerizations with the complexes are a recent phenomenon.

Late transition metal catalysts are of interest because they can be highly active and, unlike traditional early transition metal-based metallocenes, they can tolerate and incorporate polar comonomers. The most widely studied late transition metal catalysts incorporate bis(imine) ligands produced by reacting 2,6-diacylpyridines and anilines. The ligand is then combined in a separate reaction step with a suitable transition metal source to give the desired complex. The two-step preparation of a tridentate complex from 2,6-diacetylpyridine, 2,4,6-trimethylaniline, and $FeCl_2$ is typical:

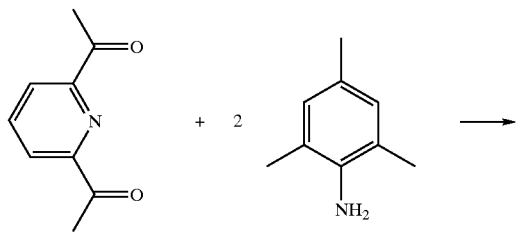

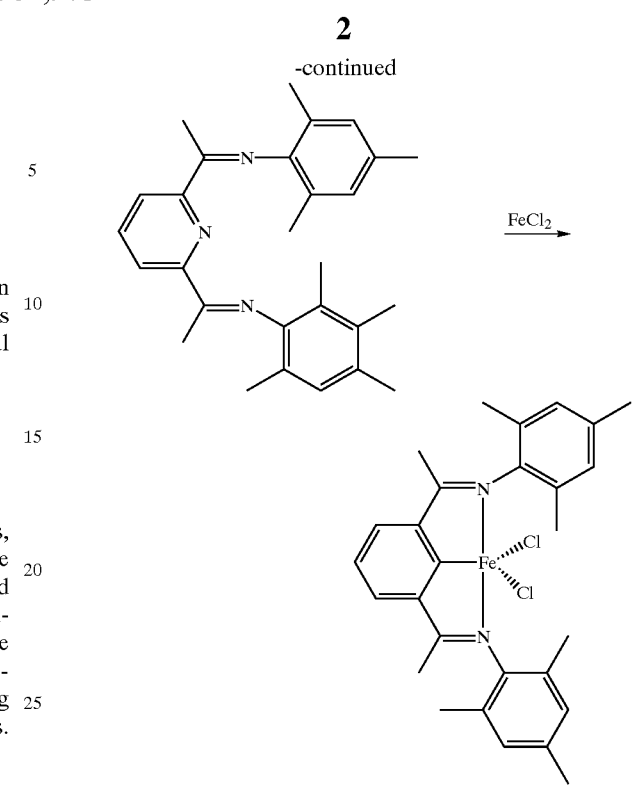

The two reaction steps are normally performed separately. The bis(imine) is prepared in one flask and is isolated. Subsequently, the bis(imine) is combined in another reaction vessel with the transition metal source to give the desired complex. For typical preparations, see U.S. Pat. No. 5,955,555 (Examples 1 and 11) and PCT Int. Appl. WO 99/12981 (Examples 4.1, 4.2, 9.1, and 9.2).

A drawback of the current methods for making these complexes is that the overall yield for the two-step process is often less than 50%. See, e.g., WO 99/12981, examples 9.1 and 9.2, where the overall yield from the two steps is 60%×64%=38.4%. Our own comparisons using the published two-step procedures (see Comparative Examples 7 and 9 below), gave results consistent with the published yields, and the results did not change significantly by changing the reaction solvent, catalyst, or reaction conditions (temperature, time). For example, we obtained about a 40% yield when using either the two-step, two-reactor procedure of the '555 patent (imine preparation in methanol using catalytic formic acid, complex preparation in THF, both at room temperature) or the two-step, two-reactor procedure of WO 99/12981 (acetic acid, refluxing ethanol for imine preparation; complex made in refluxing 1-butanol).

In view of the accelerating importance of highly active Group VIII metal bis(imine) complexes to polyolefin makers, finding ways to produce them in high yields (e.g., greater than 90%) is crucial.

SUMMARY OF THE INVENTION

The invention is a one-reactor method for making late transition metal bis(imine) complexes useful for catalyzing olefin polymerizations.

In one aspect, the invention is a one-reactor method for making the complexes in a s3ingle reaction step. In this method, a 2,6-diacylpyridine, an aniline, and a Group VIII metal compound are combined and reacted in a single reaction step in a reactor that is equipped with an internal filter to give a Group VIII metal bis(imine) complex. The complex is preferably washed in the same vessel, and the wash solvent is removed through the internal filter.

In a second aspect of the invention, a one-reactor method is used to make the complexes in two reaction steps. In this method, the bis(imine) ligand is prepared first. The ligand is then reacted in the same reactor with a Group VIII transition metal compound to give the desired complex, which is preferably washed in the same vessel.

I surprisingly found that the use of a single reactor to prepare Group VIII metal bis(imine) complexes and the use of an in-reactor filter for washing the ligands and/or complexes greatly enhances the yield of complex compared with the conventional two-reactor, two-step approach in which ligand and complex are purified outside the reactor. Catalyst activity remains high. Moreover, active complexes can be made in high yield even in a single reaction step when the complex is prepared and purified in the same reactor according to the method of the invention. The method enables the efficient preparation of exceptionally high (>90%) yields of desirable Group VIII metal bis(imine) complexes.

DETAILED DESCRIPTION OF THE INVENTION

The invention provides one-reactor methods for making late transition metal complex(es. In one of these methods, the complex is made in a single reaction step. Hereinafter, this method is sometimes called the "one-reactor, one-reaction-step method." In contrast, prior-art methods are normally "two-reactor, two-reaction-step" methods. In the one-reactor methods of the invention, the bis(imine) ligand, the Group VIII metal bis(imine) complex, or both, are produced in the same reaction vessel in either one or two reaction steps. This is also known as a "one-pot" method.

In each method of the invention, a 2,6-diacylpyridine reacts with an aniline and a Group VIII metal compound to give a Group VIII metal bis(imine) complex. In the "one-reactor, one-reaction-step" method, the complex is generated in a single step, and no attempt is made to prepare or isolate a bis(imine) ligand. In the "one-reactor, two-reaction-step" method, a bis(imine) ligand is prepared first by reacting the aniline and the 2,6-diacylpyridine in the absence of the Group VIII metal compound. After the bis(imine) is prepared (and usually purified), the Group VIII metal compound is introduced, and the desired Group VIII metal bis(imine) complex is generated.

Suitable 2,6-diacylpyridines are well known. The pyridine ring can be unsubstituted or substituted with hydrocarbyl, halogen, alkoxy, aryloxy, or other functional groups that do not interfere with imine preparation, Group VIII metal complex formation, or olefin polymerization reactions. The carbonyl groups, which are attached to the 2- and 6-positions of the pyridine ring, are also attached to a hydrogen, hydrocarbyl, or substituted hydrocarbyl (e.g., haloalkyl or alkoxyalkyl) group. Preferred 2,6-diacylpyridines are 2,6-diacetylpyridine and substituted 2,6-diacetylpyridines. More examples of suitable 2,6-diacylpyridines appear in U.S. Pat. No. 5,955,555, the teachings of which are incorporated herein by reference.

Suitable anilinees are also well known. They have the general structure Ar-NH$_2$, wherein Ar is an aryl or substituted aryl group. As with the pyridines, the aniline can be substituted with hydrocarbyl, halogen, alkoxy, aryloxy, or other functional groups that do not interfere with imine preparation, Group VIII metal complex formation, or olefin polymerization reactions. Aniline and alkyl-substituted anilines, such as 2,4,6-trimethylaniline and 2,6-diethylaniline, are preferred.

The Group VIII metal compound contains a Group VIII metal in a 2+ or 3+ oxidation state. Preferred Group VIII metal compounds include iron(II), iron(III), nickel(II), cobalt(II), or the like. Suitable Group VIII metal compounds also incorporate anionic organic or inorganic groups such as halides, acetates, acetylacetonates, amides, thiocyanates, phosphines, or the like. Specific examples of suitable Group VIII metal compounds: cobalt(II) acetate, cobalt(II) acetylacetonate, cobalt(III) acetylacetonate, cobalt(II) bromide, iron(II) bromide, iron(II) chloride, iron(III) acetylacetonate, nickel(II) acetylacetonate, nickel(II) acetylacetonate, nickel(II) carbonate, nickel(II) bromide, and the like. Halides, such as cobalt(II) chloride and iron(II) chloride are particularly preferred.

The reaction product is a Group VIII metal bis(imine) complex. The bis(imine) moiety coordinates to the metal as a neutral, tridentate ligand. Thus, valence of the metal in the Group VIII metal bis(imine) complex is the same as it was in the corresponding Group VIII metal compound, i.e., 2 or 3. The anionic ligands that made up the Group VIII metal compound remain a part of the bis(imine) complex. Group VIII metal bis(imine) complexes prepared by the method of the invention are already well known. Numerous examples appear in U.S. Pat. No. 5,955,555.

Preferred complexes have the formula:

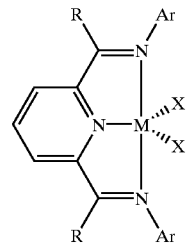

in which M is Co, Fe, or Ni; X is Cl or Br; each R is independently H or $C_1$–$C_{10}$ hydrocarbyl, and Ar is aryl or substituted aryl. Suitable complexes produced by the method of the invention include, for example, [2,6-diacetylpyridinebis(phenylimine)]cobalt(II) dichloride, [2,6-diformyl-pyridinebis(phenylimine)]iron(III) trichloride, [2,6-diacetylpyridinebis(2,4,6-trimethylphenylimine)]cobalt(II) dichloride, [2,6-diacetylpyridinebis(2,6-diethylphenylimine)]nickel(II) dibromide, [2,6-diacetyl-4-chloropyridine -bis(2,6-diisopropylphenylimine)]cobalt(II) dichloride, and the like.

The methods of the invention utilize a reactor that is equipped with an internal filter. The filter is any device capable of separating two-phase (liquid-solid) reaction mixtures provided that the separation can be accomplished within the reactor and leaves the solid phase in the reactor. Preferably, the filter is depth-flexible, i.e., its depth can be easily extended above or below the surface of the liquid phase in the reactor. While any suitable filtering device can be used, fritted glass is particularly convenient. Polymer membranes are also useful.

In a small-scale, round-bottom flask reactor, the separation might be accomplished by simply inverting the flask and pouring the liquid phase of the reaction mixture through a fritted-glass filter that is built into a sidearm of the reactor. In a preferred approach, which is illustrated below in Examples 1–6 and 8, the filter is attached to the end of a glass tube. The filter is kept above the surface of the liquid while the complex or ligand is stirred with wash solvent, and it is immersed below the liquid level for solvent removal under reduced pressure. For larger-scale glass or metal reactors, the liquid is often conveniently removed by applying pressure to the reactor contents and draining the liquid through a filter that is built into or is attached to the bottom of the reactor. Many designs for accomplishing this filtration will be readily apparent to those skilled in the art.

As noted earlier, in the "one-reaction-step" method, the complex is generated by reacting the aniline, diacylpyridine and Group VIII metal compound in a single step, and no attempt is made to prepare or isolate a bis(imine) ligand. Preferably, this method is performed in the presence of a reaction solvent. suitable reaction solvents are those capable of dissolving at least the aniline and the diacylpyridine. The Group VIII metal bis(imine) complex will usually also have good solubility in the reaction solvent. Preferred reaction solvents are relatively polar organic compounds such as alcohols, esters, ethers, amides, and ketones. Specific examples include methanol, ethanol, 1-butanol, ethyl acetate, butyl acetate, ethyl propionate, diethyl ether, N-methylpyrrolidone, N,N-dimethylformamide, acetone, methyl ethyl ketone, and the like.

While the method is performed at any desired reaction temperature, it is particularly convenient to perform it at either room temperature or at the reflux temperature of the reaction solvent. Refluxing can be used to accelerate the pace of the reaction, but better yields are sometimes obtained by opting for room temperature and a somewhat longer reaction time.

After producing the bis(imine) complex, the reaction solvent, if present, is removed from the reactor by any suitable means, including stripping, filtration, or the like, or any combination of techniques. To minimize losses of bis(imine) complex, however, the reaction mixture is preferably concentrated by stripping prior to any filtration process. Any combination of heating, vacuum stripping, and inert gas purging is used to concentrate the reaction mixture.

Preferably, the concentrated bis(imine) complex is then washed within the reactor using a wash solvent. Suitable wash solvents are organic compounds in which the bis (imine) complex has relatively limited solubility, especially when the wash solvent is cold. Examples include alcohols, ethers, esters, and aliphatic hydrocarbons. Specific examples include ethanol, methanol, diethyl ether, pentanes, hexanes, and the like. After the wash solvent is added, the complex and wash solvent are mixed well, and the wash solvent (plus impurities) is removed through the internal filter. As noted above, the wash solvent can be conveniently removed by immersing a filtering tube below the surface of the liquid and applying a vacuum to drain the solvent from the reactor through the filtering tube. Throughout this process, the complex remains inside the reactor under an inert atmosphere.

Finally, after removal any reaction solvent or wash solvent, the Group VIII metal bis(imine) complex is dried. Drying is accomplished by well-known methods, including inert gas purging, vacuum drying, mild heating, or the like, or combinations of these. The resulting dry bis(imine) complex is stored or used immediately to polymerize olefins.

As noted above, the invention includes a "one-reactor, two-reaction-step" method for making Group VIII metal bis(imine) complexes. In this method, a bis(imine) ligand is prepared first by reacting the aniline and the 2,6-diacylpyridine in the absence of the Group VIII metal compound. After the bis(imine) ligand is prepared (and usually purified), the Group VIII metal compound is introduced, and the desired Group VIII metal bis(imine) complex is generated.

The bis(imine) ligand has a well-understood structure that results from condensation of two aniline molecules and one diacylpyridine molecule. Examples appear in U.S. Pat. No. 5,955,555 (see especially col. 4). Preferred bis(imine) ligands have the structure:

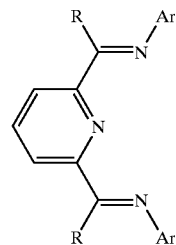

in which each R is independently H or $C_1$–$C_{10}$ hydrocarbyl, and Ar is aryl or substituted aryl.

The "one-reactor, two-reaction-step" method comprises the following steps:
(a) in a first reaction step, reacting a 2,6-diacylpyridine and an aniline in a reactor that is equipped with an internal filter, optionally in the presence of a first reaction solvent, to produce a bis(imine) ligand;
(b) removing any first reaction solvent from the reactor;
(c) optionally, drying the ligand;
(d) in a second reaction step in the same reactor, reacting the ligand with a Group VIII metal compound, optionally in the presence of a second reaction solvent, to produce a Group VIII metal bis(imine) complex;
(e) removing any second reaction solvent from the reactor; and
(f) drying the complex.

Each of steps (a)–(f) is performed in the reactor under an inert atmosphere.

Suitable 2,6-diacylpyridines, anilines, and Group VIII metal compounds for use in the two-reaction-step method have already been described above. In addition, the optional first and second reaction solvents used in the two-reaction-step method, which may be the same or different, are identical to the optional reaction solvents used in the one-reaction-step method. Removal of reaction solvent and drying of the ligand or complex are accomplished in the manner described above for the one-reaction-step method.

Preferably, the bis(imine) ligand, the Group VIII metal bis(imine) complex, or both are washed immediately following removal of any reaction solvent (i.e., immediately following steps (b) and (e), above). The washing steps are performed within the reactor under an inert atmosphere, and the wash solvent is removed through the internal filter as described above.

I surprisingly found that the yields of complexes made using the one-reactor methods of the invention are much higher than the yields obtained in the commonly used two-reactor method (see Table 1, below). Interestingly, the yield advantage applies whether the complex is made in a two reaction steps (see Examples 5, 6, and 8) or in a single reaction step (Examples 1–4). Preferably, the yield of Group VIII metal bis(imine) complex from the method of the invention is greater than 80%, and more preferably, greater than 90%. In contrast, the two-reactor method commonly gives yields of 50% or less (see Comparative Examples 7 and 9).

Complexes prepared by the methods of the invention are optionally combined with an activator to give a catalyst system useful for polymerizing olefins. Suitable activators help to ionize the organometallic complex and activate the catalyst. Suitable activators are well known in the art. Examples include alumoxanes (methyl alumoxane (MAO), PMAO, ethyl alumoxane, diisobutyl alumoxane), alkylaluminum compounds (triethilaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis(pentafluorophenyl)borate, lithium tetrakis(pentafluorophenyl)aluminate, anilinium tetrakis-pentafluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference. Suitable activators also include aluminoboronates—reaction products of alkyl aluminum compounds and organoboronic acids—as described in U.S. Pat. Nos. 5,414,180 and 5,648,440, the teachings of which are incorporated herein by reference.

The catalyst systems are optionally used with an inorganic solid or organic polymer support. Suitable supports include silica, alumina, silica-aluminas, magnesia, titania, clays, zeolites, or the like. The support is preferably treated thermally, chemically, or both prior to use to reduce the concentration of surface hydroxyl groups. Thermal treatment consists of heating (or "calcining") the support in a dry atmosphere at elevated temperature, preferably greater than about 100° C., and more preferably from about 150 to about 600° C., prior to use. A variety of different chemical treatments can be used, including reaction with organo-aluminum, -magnesium, -silicon, or -boron compounds. See, for example, the techniques described in U.S. Pat. No. 6,211,311, the teachings of which are incorporated herein by reference.

The catalyst systems are useful for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred.

Many types of olefin polymerization processes can be used. Preferably, these processes are practiced in the liquid phase, which can include slurry, solution, suspension, or bulk processes, or a combination of these. High-pressure fluid phase or gas phase techniques can also be used. Catalysts made by the methods of the invention are particularly valuable for use in solution and slurry processes.

The olefin polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 15 psig to about 50,000 psig. More preferred is the range from about 15 psig to about 1000 psig.

The following examples merely illustrate the invention. Those skilled in the art will recognize many variations that are within the spirit of the invention and scope of the claims.

EXAMPLE 1

The preceding examples are meant only as illustrations. The following claims define the invention.

Preparation of an Iron(ll) Bis(imine) Complex: "One-Reactor, One-Reaction-Step" Method A 100-mL round-bottom flask equipped with a nitrogen inlet and an internal fritted-glass filter is charged with 2,6-diacetylpyridine (2.00 g, 12.2 mmol) and ethyl acetate (50 mL). (The fritted-glass filter is attached to the end of a glass tube, which is inserted into the reactor through a rubber septum. The filter is easily raised above or lowered below the surface of liquids in the reactor.) 2,4,6-Trimethylaniline (3.52 g, 26.0 mmol, 2.13 eq.) is added to the stirred solution. The color turns from white to red within 10 min.

Iron(II) chloride (1.55 g, 12.2 mmol) is added to the flask, and the mixture is stirred under nitrogen at room temperature. The mixture turns blue within the first hour. Stirring at room temperature continues for a total of 42 h. The reaction mixture is concentrated by stripping out solvents under reduced pressure. Cold diethyl ether (30 mL) is added to the residue, and the mixture is stirred to wash the residue. The glass filter is immersed in the liquid phase, which is then removed at reduced pressure through the internal filter. The solids are dried under vacuum for 1 h.

The resulting complex, a blue powder (5.96 g, 93.1%), is collected and stored under nitrogen. $^1$H NMR (δ, $CD_2Cl_2$): 80.2 (2H, Py—$H_m$), 36.8 (1H, Py—$H_p$), 21.9 (6H, p—$CH_3$), 15.3 (4H, Ar—$H_m$), 12.1 (12H, o—$CH_3$,), −22.1 (6H, $CH_3$—C=N). FAB mass spectrum: m/z 523 [M+], 488 [M−Cl], 453 [M−2Cl].

EXAMPLE 2

The procedure of Example 1 is followed, except that 60 mL of ethyl acetate are used instead of 50 mL, and the mixture is heated to reflux (77° C.) after the iron(II) chloride is added. Refluxing continues for 10 h. The mixture is then stirred at room temperature for 32 h. The complex is washed and isolated as described above. The complex gives satisfactory $^1$H NMR and mass spectra. Yield: 5.84 g (91.3%).

EXAMPLE 3

The procedure of Example 1 is followed, except that ethanol is used as the reaction solvent instead of ethyl acetate. In addition, the mixture is stirred for a total of 120 h at room temperature following addition of the $FeCl_2$. The complex gives satisfactory $^1$H NMR and mass spectra. Yield: 5.80 g (90.6%).

EXAMPLE 4

The procedure of Example 2 is followed, except that ethanol is used as the reaction solvent instead of ethyl acetate. In addition, the refluxing step (at 78° C.) continues for 24 h, followed by stirring at room temperature for 120 h. The complex gives satisfactory $^1$H NMR and mass spectra. Yield: 5.77 g (90.2%).

EXAMPLE 5

Preparation of an Iron(II) Bis(imine) Complex: "One-Reactor, Two-Reaction-Step" Method A 100-mL round-bottom flask equipped with a nitrogen inlet and an internal fritted-glass filter is charged with 2,6-diacetylpyridine (2.00 g, 12.2 mmol) and ethyl acetate (30 mL). 2,4,6-Trimethylaniline (3.52 g, 26.0 mmol, 2.13 eq.) and formic acid (4 drops) are added. The solution is stirred at room temperature under nitrogen for 1 h, and is then heated to reflux for 24 h. The reaction solvent is stripped and the solids are dried under vacuum in the reactor flask for 2 h. A sample of the bis(imine) compound is withdrawn for NMR analysis ($^1$H NMR, CDCl$_{3, \delta}$: 2.05 (s, 12H); 2.28 (s, 6H), 2.33 (s, 6H), 6.94 (s, 4H), 7.95 (t, 1H), 8.5 (d, 2H)).

In the same flask, tetrahydrofuran (40 mL) is added to the bis(imine) solids, and the mixture is stirred for 0.5 h. Iron(II) chloride (1.55 g, 12.2 mmol) is added to the flask, and the mixture is stirred under nitrogen at room temperature for 15 h. A blue solid precipitates. The liquid phase is removed by filtration (internal filter). The residue is washed with cold ethanol (20 mL), and the washings are removed by filtration at reduced pressure through the internal filter. The resulting solids are dried under vacuum for 1 h. The complex gives satisfactory $^1$H NMR and mass spectral. Yield: 5.86 g (91.6%).

EXAMPLE 6

Preparation of an Iron(ll) Bis(imine) Complex: "One-Reactor, Two-Reaction-Step" Method The method of U.S. Pat. No. 5,955,555 is generally followed, but is modified in accordance with the one-reactor method of the invention. Thus, a 100-mL round-bottom flask equipped with a nitrogen inlet and an internal fritted-glass filter is charged with 2,6-diacetylpyridine (2.00 g, 12.2 mmol) and methanol (30 mL). 2,4,6-Trimethylaniline (3.47 g, 25.7 mmol, 2.10 eq.) and formic acid (3 drops) are added. The solution is stirred at room temperature under nitrogen for 48 h, and yellow precipitate is observed. The liquid phase is removed by filtration (internal filter), and the solids are dried under vacuum in the reactor flask for 1 h. Analysis of a sample of the bis(imine) compound gives a satisfactory $^1$H NMR spectrum.

In the same flask, tetrahydrofuran (30 mL) is added to the bis(imine) solids, and the mixture is stirred for 0.5 h. Iron(II) chloride (1.55 g, 12.2 mmol) is added to the flask, and the mixture is stirred for 18 h under nitrogen at room temperature. A blue solid precipitates. The mixture is concentrated to a few mL volume, and the precipitate is then washed with cold diethyl ether (10 mL). The liquid phase is removed by filtration (internal filter). The residue is washed with cold pentane (3×10 mL), and each washing is removed by filtration at reduced pressure through the internal filter. The resulting solids are dried under vacuum for 1 h. The complex gives satisfactory $^1$H NMR and mass spectra. Yield: 5.82 g (90.9%)

Comparative Example 7

Preparation of an Iron(II) Bis(imine) Complex: Two-Reactor Method

The two-reactor method of U.S. Pat. No. 5,955,555 is generally followed. Thus, a 100-mL round-bottom flask equipped with a nitrogen inlet is charged with 2,6-diacetylpyridine (2.00 g, 12.2 mmol) and methanol (30 mL). 2,4,6-Trimethylaniline (3.47 g, 25.7 mmol, 2.10 eq.) and formic acid (3 drops) are added. The solution is stirred at room temperature under nitrogen for 48 h, and yellow precipitate is observed. The mixture is filtered (outside the reactor), and the solids are washed with cold methanol (15 mL). Analysis of a sample of the bis(imine) compound gives a satisfactory $^1$H NMR spectrum. Yield: 3.39 g (70.0%).

In a separate 100-mL round-bottom flask, tetrahydrofuran (30 mL) is added to the bis(imine) solids (3.39 g, 8.54 mmol), and the mixture is stirred for 0.5 h. Iron(II) chloride (1.08 g, 8.54 mmol) is added to the flask, and the mixture is stirred for 18 h under nitrogen at room temperature. A blue solid precipitates. The mixture is filtered (outside the reactor), and the solids are washed with cold pentane (3×10 mL). The resulting solids are dried under vacuum for 2 h. The complex gives satisfactory $^1$H NMR and mass spectra. Yield: 2.69 g (60.0%). Overall yield for both steps is 42%.

EXAMPLE 8

Preparation of an Iron(Ii) Bis(imine) Complex: "One-Reactor, Two-Reaction-Step" Method The method of PCT Int. Publ. WO 99/12981 is generally followed, but is modified in accordance with the one-reactor method of the invention. Thus, a 200-mL round-bottom flask equipped with a nitrogen inlet and an internal fritted-glass filter is charged with 2,6-diacetylpyridine (2.50 g, 15.3 mmol) and absolute ethanol (100 mL). 2,4,6-Trimethylaniline (4.14 g, 30.6 mmol, 2.50 eq.) and glacial acetic acid (4 drops) are added. The solution is stirred at room temperature under nitrogen for 1 h, and is then refluxed (78° C.) for 15 h. A yellow precipitate is observed. The mixture is cooled to room temperature, and the ethanol phase is removed by filtration (internal filter). The solids are dried under vacuum in the reactor flask for 2 h. Analysis of a sample of the bis(imine) compound gives a satisfactory $^1$H NMR spectrum.

In the same flask, 1-butanol (30 mL) is added to the bis(imine) solids (about 15.3 mmol), followed by iron(II) chloride (1.94 g, 15.3 mmol). The mixture is heated at reflux (80° C.) under nitrogen for 1 h, followed by stirring at room temperature for 18 h. The mixture is concentrated to a few mL volume, and the blue precipitate is washed with cold diethyl ether (15 mL). The liquid phase is removed by filtration (internal filter). The residue is washed with cold diethyl ether (3×10 mL), and the washings are removed by filtration at reduced pressure through the internal filter. The resulting solids are dried under vacuum for 1 h. The complex gives satisfactory $^1$H NMR and mass spectra. Yield: 7.32 g (91.1%).

Comparative Example 9

Preparation of an Iron(II) Bis(imine) Complex: Two-Reactor Method

The method of PCT Int. Publ. WO 99/12981 is generally followed. Thus, a 200-mL round-bottom flask equipped with a nitrogen inlet is charged with 2,6-diacetylpyridine (2.50 g, 15.3 mmol) and absolute ethanol (100 mL). 2,4,6-Trimethylaniline (4.14 g, 30.6 mmol, 2.50 eq.) and glacial acetic acid (4 drops) are added. The solution is stirred at room temperature under nitrogen for 1 h, and is then refluxed (78° C.) for 15 h. A yellow precipitate is observed. The mixture is cooled to room temperature and filtered (outside the reactor). The solids are washed with cold ethanol (15 mL) and dried at 50° C. under vacuum for 16 h. Analysis of a sample of the bis(imine) compound gives a satisfactory $^1$H NMR spectrum. Yield: 3.71 g (61.0%).

In a separate 100-mL round-bottom flask, iron(Ii) chloride (0.27 g 2.13 mmol), 1-butanol (30 mL) and a portion of the bis(imine) compound (0.847 g, 2.13 mmol) are combined and stirred for 5 min. The mixture is heated at reflux (80° C.) under nitrogen for 1 h, and is then stirred for 18 h under nitrogen at room temperature. Most of the reaction solvent is removed by stripping, and cold diethyl ether (15 mL) is added to precipitate the blue complex. The mixture is filtered (outside the reactor), and the solids are washed with cold diethyl ether (3×10 mL). The resulting solids are dried under vacuum for 1 h. The complex gives satisfactory $^1$H NMR and mass spectra. Yield: 0.717 g (64.0%). Overall yield for both steps is 39%.

Ethylene Polymerization

All polymerizations are performed at 80° C. in a 2-liter slurry reactor using isobutane as a solvent. The reactor is pre-conditioned by heating it to 120° C. and holding it at that temperature for 20 min. under a nitrogen purge. Ethylene, isobutane, hydrogen, and nitrogen are dried prior to use with 13X molecular sieves.

For a typical polymerization, the desired amount of hydrogen (ΔP=5 psi) is added to the reactor by monitoring the pressure drop from a 300-mL steel vessel pressurized with hydrogen. Then, isobutane (550 mL) is charged into the reactor. Ethylene is introduced into the reactor on demand using a Brooks mass flow meter set at 400 psi. In the reactor, ethylene pressure is 290 psi (about 20 bar), and hydrogen pressure is 0–5 psi. The concentration of ethylene in isobutane is about 15 mol %.

A small amount of triisobutylaluminum solution (2.7 mL of 1.0 M solution in hexane) is charged from a first injector into the reactor to scavenge trace amounts of moisture in the system. The desired amounts of catalyst (1 to 5 mg of complex) and cocatalyst (MAO solution in toluene; [Al:Fe] molar ratio=50 to 200) are then added to the reactor from a second injector to initiate the polymerization. The reactor is kept at 80° C. throughout the polymerization. When the reaction is completed (15 to 60 min.), the reactor is vented and the resulting polyethylene is collected and dried at 50° C. under vacuum. Catalyst activities are reported in Table 1.

As Table 1 shows, the activities of catalysts prepared by the method of the invention are as high (or slightly higher) than those of catalysts made in the conventional two-reactor approach. Surprisingly, however, the % yields of complexes made using the one-reactor approach are much higher than the yields obtained in the two-reactor method. Interestingly, the yield advantage applies whether the complex is made in a two reaction steps (Examples 5, 6, and 8) or in a single reaction step (Examples 1–4).

TABLE 1

Summary of Results
One-Reactor Method for Making Late Transition Metal Bis(imine) Complexes

| ex # | # reactors | # rxn steps | conditions (see examples for all details) | yield of complex (%) | activity (kg PE/g Fe/h) |
|---|---|---|---|---|---|
| 1 | 1 | 1 | EtOAc, RT | 93.1 | 1200 |
| 2 | 1 | 1 | EtOAc, reflux | 91.3 | 1020 |
| 3 | 1 | 1 | EtOH, RT | 90.6 | 1000 |
| 4 | 1 | 1 | EtOH, reflux | 90.2 | 900 |
| 5 | 1 | 2 | 1) EtOAc, formic acid, RT 2) THF, RT | 91.6 | 980 |
| 6 | 1 | 2 | 1) MeOH, formic acid, RT 2) THF, RT | 90.9 | 950 |
| C7 | 2 | 2 | 1) MeOH, formic acid, RT 2) THF, RT | 42.0 | 910 |
| 8 | 1 | 2 | 1) EtOH, acetic acid, reflux 2) BuOH, reflux | 91.1 | 920 |
| C9 | 2 | 2 | 1) EtOH, acetic acid, reflux 2) BuOH, reflux | 38.4 | 880 |

I claim:

1. A method which comprises:
   (a) reacting a 2,6-diacylpyridine, an aniline, and a Group VIII metal compound selected from the group consisting of iron(II) and cobalt(II) compounds, in one reaction step in a single reactor that is equipped with an internal filter, optionally in the presence of a reaction solvent, to produce an iron(II) or cobalt(II) bis(imine) complex;
   (b) removing any reaction solvent from the reactor; and
   (c) drying the complex;
   wherein each of steps (a)–(c) is performed in the reactor under an inert atmosphere.

2. The method of claim 1 wherein the 2,6-diacylpyridine is 2,6-diacetylpyridine.

3. The method of claim 1 wherein the aniline is 2,4,6-trimethylaniline.

4. The method of claim 1 wherein the Group VIII metal compound is selected from the group consisting of $FeCl_2$ and $CoCl_2$.

5. The method of claim 1 wherein step (a) is performed at room temperature.

6. The method of claim 1 wherein step (a) is performed at the reflux temperature of the reaction solvent.

7. The method of claim 1 wherein step (b) is accomplished by stripping, filtration, or a combination thereof.

8. The method of claim 1 wherein the yield of iron(II) or cobalt(II) bis(imine) complex is greater than 90%.

9. The method of claim 1 further comprising, after step (b) and before step (c): adding a wash solvent to the reactor and mixing it with the complex; and removing the wash solvent through the internal filter.

10. The method of claim 9 wherein the wash solvent is selected from the group consisting of alcohols, ethers, esters, and aliphatic hydrocarbons.

11. A method which comprises:
   (a) in a first reaction step, reacting a 2,6-diacylpyridine and an aniline in a reactor that is equipped with an internal filter, optionally in the presence of a first reaction solvent, to produce a bis(imine) ligand;
   (b) removing any first reaction solvent from the reactor;
   (c) optionally, drying the ligand;
   (d) in a second reaction step in the same reactor, reacting the ligand with a Group VIII metal compound selected from the group consisting of iron(II) and cobalt(II) compounds, optionally in the presence of a second reaction solvent, to produce iron(II) or cobalt(II) bis(imine) complex;
   (e) removing any second reaction solvent from the reactor; and
   (f) drying the complex;
   wherein each of steps (a)–(f) is performed in the reactor under an inert atmosphere.

12. The method of claim 11 wherein the 2,6-diacylpyridine is 2,6-diacetylpyridine.

13. The method of claim 11 wherein the aniline is 2,4,6-trimethylaniline.

14. The method of claim 11 wherein the Group VIII metal compound is selected from the group consisting of $FeCl_2$ and $CoCl_2$.

15. The method of claim 11 wherein steps (a) and (d) are performed at room temperature.

16. The method of claim 11 wherein steps (a) and (d) are performed at the reflux temperatures of the first and second reaction solvents.

17. The method of claim 11 wherein each of steps (b) and (e) is accomplished by stripping, filtration, or a combination thereof.

18. The method of claim 11 wherein the yield of iron(II) or cobalt(II) bis(imine) complex is greater than 90%.

19. The method of claim 11 further comprising, after step (b) and before step (c): adding a first wash solvent to the reactor and mixing it with the complex; and removing the first wash solvent through the internal filter.

20. The method of claim 19 wherein the first wash solvent is selected from the group consisting of alcohols, ethers, esters, and aliphatic hydrocarbons.

21. The method of claim 11 further comprising, after step (e) and before step (f): adding a second wash solvent to the reactor and mixing it with the complex; and removing the second wash solvent through the internal filter.

22. The method of claim 21 wherein the second wash solvent is selected from the group consisting of alcohols, ethers, esters, and aliphatic hydrocarbons.

* * * * *